United States Patent
Haase et al.

(10) Patent No.: US 11,432,794 B2
(45) Date of Patent: Sep. 6, 2022

(54) BLOOD FLOW DETERMINATION APPARATUS

(71) Applicant: KONINKLIJKE PHILIPS N. V., Eindhoven (NL)

(72) Inventors: Christian Haase, Hamburg (DE); Michael Grass, Buchholz in der Nordheide (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 638 days.

(21) Appl. No.: 16/336,331

(22) PCT Filed: Sep. 18, 2017

(86) PCT No.: PCT/EP2017/073380
§ 371 (c)(1),
(2) Date: Mar. 25, 2019

(87) PCT Pub. No.: WO2018/059976
PCT Pub. Date: Apr. 5, 2018

(65) Prior Publication Data
US 2019/0223829 A1    Jul. 25, 2019

(30) Foreign Application Priority Data
Sep. 28, 2016   (EP) ..................................... 16191056

(51) Int. Cl.
*A61B 8/06*   (2006.01)
*A61B 8/12*   (2006.01)
(Continued)

(52) U.S. Cl.
CPC .................. *A61B 8/06* (2013.01); *A61B 8/12* (2013.01); *A61B 8/445* (2013.01); *A61B 5/026* (2013.01)

(58) Field of Classification Search
None
See application file for complete search history.

(56) References Cited

U.S. PATENT DOCUMENTS

2002/0065467 A1   5/2002   Schutt
2003/0216681 A1*  11/2003  Zhang ..................... A61M 5/14
                                                                    604/22
(Continued)

FOREIGN PATENT DOCUMENTS

CA       2873391 A1      11/2013
WO    2013177527 A1      11/2013

OTHER PUBLICATIONS

Wang, L. et al., "Contrast medium assisted fluid flow measurements", IEEE Transactions on Ultrasonics, Ferroelecliics and Frequency Control, vol. 42, No. 2, Mar. 1995.
(Continued)

*Primary Examiner* — Shahdeep Mohammed

(57) ABSTRACT

The invention relates to a blood flow determination apparatus (5) comprising a speckle density determination unit (7) for determining a speckle density value being indicative of a level of a speckle density in an ultrasound image of an inner lumen of a blood vessel, which has been generated at an imaging location being behind an introduction location at which a fluid has been introduced into the blood vessel (20) with a known volumetric fluid flow rate. A blood flow rate determination unit (8) determines a blood flow value being indicative of a volumetric blood flow rate based on the determined speckle density value and the volumetric fluid flow rate. This allows determining the intravascular blood flow with an improved accuracy.

24 Claims, 11 Drawing Sheets

(51) Int. Cl.
*A61B 5/026* (2006.01)
*A61B 8/00* (2006.01)

(56) References Cited

U.S. PATENT DOCUMENTS

| | | | | |
|---|---|---|---|---|
| 2005/0015009 A1* | 1/2005 | Mourad | ............... | A61B 5/7267 |
| | | | | 600/438 |
| 2011/0034801 A1* | 2/2011 | Baumgart | .............. | A61B 6/463 |
| | | | | 600/411 |
| 2013/0072907 A1* | 3/2013 | Lichty, II | ............... | A61B 17/12 |
| | | | | 604/528 |
| 2013/0317359 A1* | 11/2013 | Wilson | ................... | A61B 5/027 |
| | | | | 600/425 |

OTHER PUBLICATIONS

Leow, C. et al., "Flow Velocity Mapping Using Contrast Enhanced High-Frame-Rate Plane Wave Ultrasound and Image Tracking: Methods and Initial in Vitro and in Vivo Evaluation", Ultrasound in Med. & Biol., vol. 41, No. 11, pp. 2913-2925, 2015.

\* cited by examiner

BLOOD FLOW DETERMINATION APPARATUS

CROSS-REFERENCE TO PRIOR APPLICATIONS

This application is the U.S. National Phase application under 35 U.S.C. § 371 of International Application No. PCT/EP2017/073380, filed on 18 Sep. 2017, which claims the benefit of European Patent Application No. 16191056.7, filed on 28 Sep. 2016. These applications are hereby incorporated by reference herein.

FIELD OF THE INVENTION

The invention relates to a blood flow determination apparatus, method and computer program. The invention relates further to a blood flow determination system comprising the blood flow determination apparatus, a fluid introduction unit and an ultrasound unit, and to an angiography image generation system for generating an angiography image, wherein the angiography image generation system comprises the blood flow determination system.

BACKGROUND OF THE INVENTION

WO 2013/177527 A1 discloses a system with a catheter assembly which includes an intravascular measuring device having a measurement module configured to emit and receive energy and to generate measurement data, wherein the catheter assembly is configured to introduce a quantity of fluid into a vessel of a patient. The system further comprises a measurement engine in communication with the intravascular measuring device, wherein the measurement engine is configured to receive the measurement data from the intravascular measuring device, to determine a start time associated with the introduction of the quantity of fluid into a predetermined portion of the vessel, and to determine an end time based on the measurement data. The measurement engine is further configured to calculate an elapsed time based on the start time and the end time and to calculate a blood flow velocity through the vessel based on the elapsed time and a travel distance of the quantity of fluid during the elapsed time. Since the quality of determining the travel distance and/or the elapsed time is often not very high, the accuracy of determining the blood flow velocity can be relatively low. Moreover, in many applications the volumetric blood flow rate is more relevant than the blood flow velocity.

SUMMARY OF THE INVENTION

It is an object of the present invention to provide a blood flow determination apparatus, method and computer program which allow an accurate determination of a blood flow value being indicative of a volumetric blood flow rate within a blood vessel. It is a further object of the present invention to provide a blood flow determination system comprising the blood flow determination apparatus, a fluid introduction unit and an ultrasound unit, and to provide an angiography image generation system for generating an angiography image which comprises the blood flow determination system.

In a first aspect of the present invention a blood flow determination apparatus is presented, wherein the blood flow determination apparatus comprises:

a speckle density determination unit for determining a speckle density value being indicative of a level of a speckle density in an ultrasound image of an inner lumen of a blood vessel, which has been generated at an imaging location being behind an introduction location with respect to a flow direction of blood within the blood vessel, wherein at the introduction location a fluid has been introduced into the blood vessel with a known volumetric fluid flow rate, a blood flow rate determination unit for determining a blood flow value being indicative of a volumetric blood flow rate based on the determined speckle density value and the volumetric fluid flow rate.

Since the blood flow determination unit is adapted to determine the blood flow value based on the determined speckle density value which is indicative of the level of the speckle density, i.e. the amount of the speckle density, in the ultrasound image and based on the known volumetric fluid flow rate and since the speckle density value in the ultrasound image can be determined very accurately, the blood flow can be determined with an improved accuracy. In particular, it is not necessary to determine, for instance, an elapsed time and a travel distance for determining the blood flow value.

The blood flow rate determination unit is preferentially adapted to use directly the speckle density value for determining the blood flow value being indicative of the volumetric blood flow rate, i.e. preferentially the speckle density value itself is used for this determination. For instance, a function can be provided which defines the blood flow value based on the speckle density value and the volumetric fluid flow rate. This particularly means that the speckle density value is preferentially not used for detecting a time at which the speckle density decreases or increases in an ultrasound image by, for instance, thresholding the speckle density value and that this time is used for determining the blood flow value. Moreover, the known volumetric fluid flow rate is preferentially a volumetric fluid flow rate of a continuous introduction of the fluid into the blood vessel, i.e. preferentially the fluid is continuously introduced and not, for instance, as a fluid bolus only. The volumetric fluid flow rate is preferentially constant.

The speckle density determination unit is preferentially adapted to determine the speckle density value based on the image values of the ultrasound image. In particular, the speckle density determination unit is adapted to determine the speckle density value by adding the image values, which might be grey values, within a region of the ultrasound image, which corresponds to the inner lumen of the blood vessel, and by dividing the resulting sum by the area of this region.

In an embodiment the blood flow determination apparatus further comprises a speckle density providing unit for providing a blood speckle density value being indicative of the level of the speckle density in an ultrasound image only showing blood and for providing a fluid speckle density value being indicative of the level of the speckle density in an ultrasound image only showing the fluid, wherein the blood flow rate determination unit is adapted to determine the blood flow value also based on the blood speckle density value and the fluid speckle density value. In particular, the speckle density providing unit is adapted to determine the blood speckle density value based on a further ultrasound image of the inner lumen of the blood vessel, which has been generated at a location at which the inner lumen of the blood vessel only contains blood. For instance, the further ultrasound image can be generated at the imaging location, before the fluid is introduced into the blood vessel, in order to generate the further ultrasound image at a location at which the inner lumen of the blood vessel only contains blood. The speckle density providing unit can also be a storing unit in which the blood speckle density value is stored already and from which the blood speckle density value can be retrieved for providing the same. Also the fluid speckle density value can be stored already in the speckle density providing unit, in order to allow the speckle density providing unit to provide the stored fluid speckle density value. The speckle density providing unit can also be adapted to receive an ultrasound image just showing the fluid and to determine the fluid speckle density value based on this ultrasound image. By using the blood speckle density value and the fluid speckle density value for determining the blood flow the accuracy of determining the blood flow can be further increased.

Preferentially, the speckle density determination unit is adapted to determine the speckle density value such that it is indicative of an average of levels of speckle densities in at least some of several ultrasound images which have been generated for different times at the imaging location, while the fluid has been continuously introduced into the blood vessel. Thus, a fluid introduction unit can be adapted to continuously introduce the fluid into the blood vessel with the known volumetric fluid flow rate, while an ultrasound unit generates several ultrasound images for different times at the imaging location, and the speckle density value can be determined such that it is indicative of an average of levels of speckle densities in some or all of these several ultrasound images. This temporal averaging can lead to a further improved accuracy of determining the speckle density value and hence of the blood flow value being indicative of the volumetric blood flow rate.

The speckle density determination unit is preferentially adapted to consider the entire region of the ultrasound image, which corresponds to the inner lumen of the blood vessel, for determining the speckle density value. Thus, a relatively large region of the ultrasound image is used for determining the speckle density value, thereby reducing the likelihood that generally possible local inaccuracies diminish the accuracy of the determination of the speckle density value. Also this allows for an improved accuracy of determining the speckle density value and hence of the blood flow value.

It is further preferred that the blood flow rate determination unit is adapted to use a non-linear relation between the blood flow value to be determined and the speckle density value. In particular, the blood flow rate determination unit is adapted to use following non-linear relation between the blood flow value to be determined and the speckle density value:

$$Q_B = Q_C(\theta_M - \theta_C)/(\theta_B - \theta_M) = Q_C(f(d_M) - f(d_C))/(f(d_B) - f(d_M)),$$

wherein $Q_B$ denotes the blood flow value to be determined, $Q_C$ denotes the volumetric fluid flow rate at the introduction location, $\theta_M$ denotes a scatterer concentration value being indicative of the concentration of ultrasound scatterers in the mix of blood and fluid in the inner lumen of the blood vessel at the imaging location, $\theta_C$ denotes a fluid scatterer concentration value being indicative of the concentration of ultrasound scatterers in the fluid, $\theta_B$ denotes a blood scatterer concentration value being indicative of the concentration of ultrasound scatterers in the fluid, $d_M$ denotes the speckle density value being indicative of the level of the speckle density in the ultrasound image of the inner lumen of the blood vessel which has been generated at the imaging location, $d_C$ denotes the provided fluid speckle density value and $d_B$ denotes the provided blood density speckle value.

Moreover, f(d) is a non-linear function relating an ultrasound speckle density value d to a corresponding scatterer concentration θ. This function can be, for instance, a phenomenologically calibrated function or can be derived from analytical calculations or numerical computer models. By using the non-linear relation between the blood flow value to be determined and the speckle density value, particularly between the scatterer concentration and the speckle density value, the accuracy of determining the blood flow value can be further increased.

In a further aspect of the present invention a blood flow determination system is presented, wherein the blood flow determination system comprises:

a fluid introduction unit for introducing a fluid into the blood vessel with a volumetric fluid flow rate at an introduction location, an ultrasound unit for generating an ultrasound image of an inner lumen of the blood vessel at an imaging location being behind the introduction location with respect to a flow direction of the blood within the blood vessel, and blood flow determination apparatus for determining a blood flow value being indicative of a volumetric blood flow rate within a blood vessel as defined in claim 1. Preferentially, the ultrasound unit comprises an intravascular ultrasound (IVUS) probe for generating the ultrasound image of the inner lumen of the blood vessel.

In an embodiment the fluid introduction unit comprises a tube with several tube openings located along the length of the tube for introducing the fluid into the blood vessel at several introduction locations with a respective known volumetric fluid flow rate, wherein the ultrasound unit is adapted to determine for each introduction location a respective ultrasound image of the inner lumen of the blood vessel at an imaging location being behind the respective introduction location with respect to the flow direction of the blood within the blood vessel, wherein the speckle density determination unit is adapted to determine for each ultrasound image a respective speckle density value being indicative of the level of the speckle density in the respective ultrasound image, and wherein the blood flow rate determination unit is adapted to determine several blood flow values being indicative of several volumetric blood flow rates based on the determined several speckle density values and the volumetric fluid flow rates. This allows for a determination of several blood flow values along the length of the tube and hence along the length of the blood vessel, in which the tube is located, without necessarily requiring a movement of the tube. It is therefore possible to accurately determine a spatial distribution of blood flow in a relatively simple way.

The ultrasound unit can comprise an IVUS probe, which is arrangable behind all of the several tube openings with respect to the flow direction of the blood within the blood vessel. In this case the fluid introduction unit can be adapted to temporarily sequentially introduce the fluid into the blood vessel at the several introduction locations such that at a respective point in time the fluid is introduced into the blood vessel at a single introduction location only, wherein the ultrasound unit with the IVUS probe can be adapted to determine at the respective point in time a respective ultrasound image of the inner lumen of the blood vessel at an imaging location, at which the IVUS probe is located and which is arranged behind all of the several tube openings, in order to determine for the respective introduction location the respective ultrasound image.

In a further embodiment the ultrasound unit is adapted to determine several ultrasound images at several imaging locations, wherein behind each introduction location a respective imaging location is arranged, i.e. pairs of a respective introduction location and a respective imaging location are arranged behind each other. Also in this case the speckle density determination unit is adapted to determine for each ultrasound image a respective speckle density value being indicative of the respective level of the speckle density in the respective ultrasound image, wherein the blood flow rate determination unit is adapted to determine several blood flow values being indicative of several volumetric blood flow rates based on the determined several speckle density values and the volumetric fluid flow rates. In particular, for determining a blood flow value for a respective introduction location a) the speckle density value determined for the ultrasound image generated at the imaging location immediately behind the introduction location, b) the volumetric fluid flow rate with which the fluid has been introduced into the blood vessel at the respective introduction location and, if one or several introduction locations are arranged in front of the respective introduction location for which the respective blood flow value is to be determined, c) also the one or more volumetric fluid flow rates with which the fluid has been introduced at the one or several previous introduction location are considered. In this embodiment the fluid can be introduced through the several tube openings into the blood vessel simultaneously, in order to determine a spatial distribution of blood flow values along the length of the tube and hence along the length of the blood vessel.

In an embodiment the ultrasound unit comprises several IVUS probes for generating several ultrasound images of the inner lumen of the blood vessel at several imaging locations being behind the introduction location with respect to the flow direction of the blood within the blood vessel, wherein the speckle density determination unit is adapted to determine several speckle density values being indicative of the levels of the speckle densities of the respective ultrasound images and wherein the blood flow rate determination unit is adapted to determine the blood flow value being indicative of the volumetric blood flow rate based on an average of the determined several speckle density values and the volumetric fluid flow rate. This can further improve the quality of the determined blood flow value.

In a further aspect of the present invention an angiography image generation system for generating an angiography image is presented, wherein the angiography image generation system comprises:

a blood flow determination system as defined in claim 8, wherein the fluid introduction unit is adapted to introduce a contrast agent as the fluid into the blood vessel, a contrast agent imaging unit for generating an image of the contrast agent within the blood vessel, in order to generate the angiography image.

Thus, the same fluid can be used for determining the blood flow value and for generating the angiography image, thereby allowing for an accurate determination of the blood flow value and a generation of an angiography image in a same procedure. Moreover, the time needed for accurately determining the blood flow value and for generating the angiography image can thereby be significantly reduced.

In a further aspect of the present invention a blood flow determination method is presented, wherein the blood flow determination method comprises:

determining a speckle density value being indicative of a level of a speckle density in an ultrasound image of an inner lumen of a blood vessel, which has been generated at an imaging location being behind an introduction location with respect to a flow direction of blood within the blood vessel, wherein at the introduction location a fluid has been introduced into the blood vessel with a known volumetric fluid flow rate, by a speckle density determination unit, and determining a blood flow value being indicative of a volumetric blood flow rate based on the determined speckle density value and the volumetric fluid flow rate by a blood flow rate determination unit.

In another aspect of the present invention an angiography image generation method is presented, wherein the angiography image generation method comprises:

carrying out the steps of the blood flow determination method as defined in claim 13, wherein a contrast agent is introduced into the blood vessel as the fluid, generating an image of the contrast agent within the blood vessel by a contrast agent imaging unit, in order to generate the angiography image.

In a further aspect of the present invention a blood flow determination computer program is presented, wherein the blood flow determination computer program comprises program code means for causing a blood flow determination apparatus as defined in claim 1 to carry out the blood flow determination method as defined in claim 13, when the computer program is run on the blood flow determination apparatus.

It shall be understood that the blood flow determination apparatus of claim 1, the blood flow determination system of claim 8, the angiography image generation system of claim 12, the blood flow determination method of claim 13, the angiography image generation method of claim 14 and the blood flow determination computer program of claim 15 have similar and/or identical preferred embodiments, in particular, as defined in the dependent claims.

It shall be understood that a preferred embodiment of the present invention can also be any combination of the dependent claims or above embodiments with the respective independent claim.

These and other aspects of the invention will be apparent from and elucidated with reference to the embodiments described hereinafter.

DETAILED DESCRIPTION OF EMBODIMENTS

Figure 1:
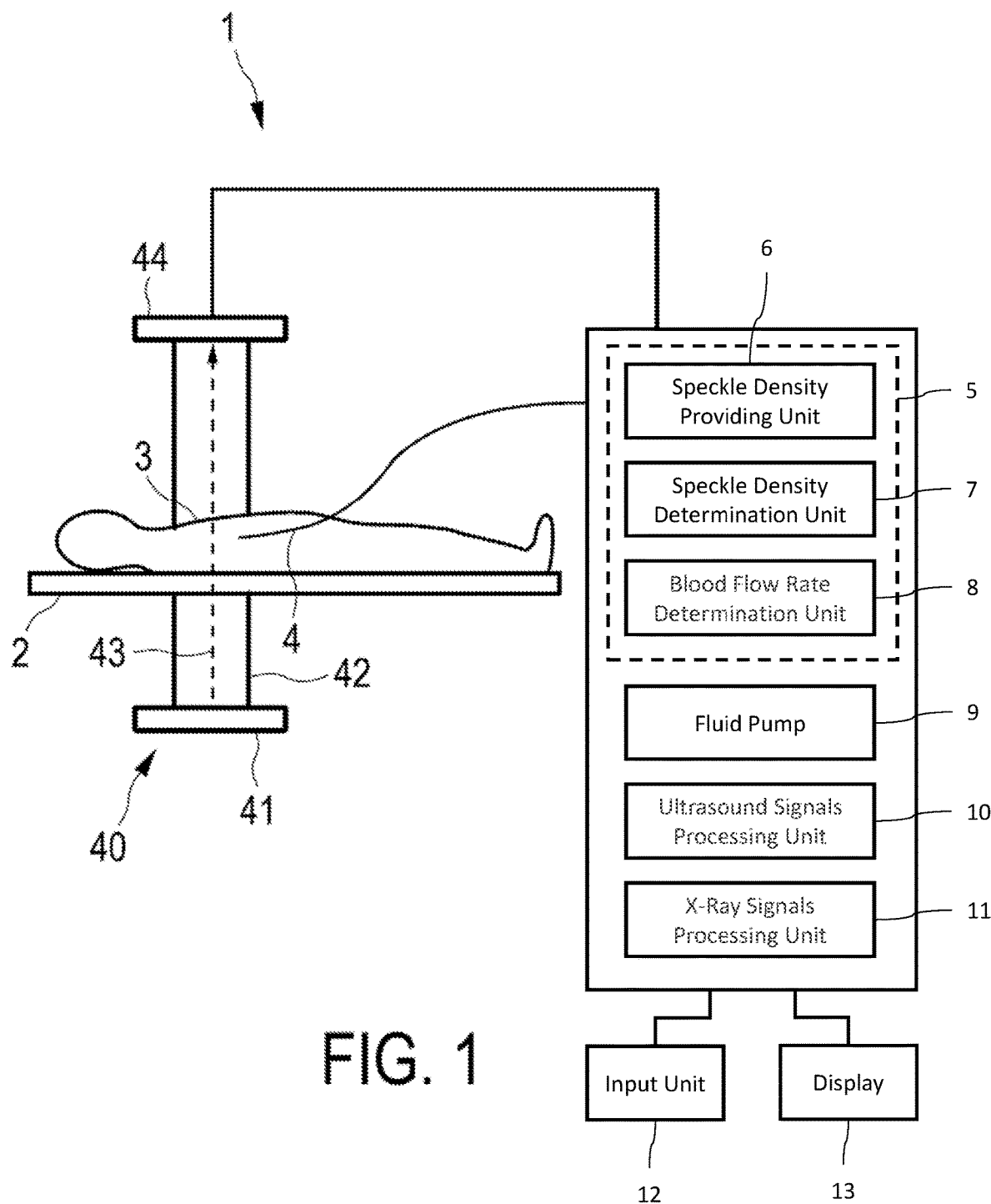
FIG. 1 shows schematically and exemplarily an embodiment of an angiography image generation system.

FIG. 1 shows schematically and exemplarily an embodiment of an angiography image generation system 1 for generating an angiography image. The angiography image generation system 1 comprises an x-ray device 40 including an x-ray source 41 for emitting x-rays 43 and an x-ray detector 44 for generating x-ray signals being indicative of the intensity of the x-rays 43 after having traversed a patient 3 lying on a patient table 2. The x-ray source 41 and the x-ray detector 44 are attached to opposing ends of a C-arm 42 which is movable with respect to the patient 3. In particular, the C-arm 42 is rotatable around a longitudinal axis of the patient 3, in order to allow the x-ray device 40 to generate x-ray signals being indicative of the intensity of the x-rays 43 after having traversed the patient 3 in different directions.

Figure 2:
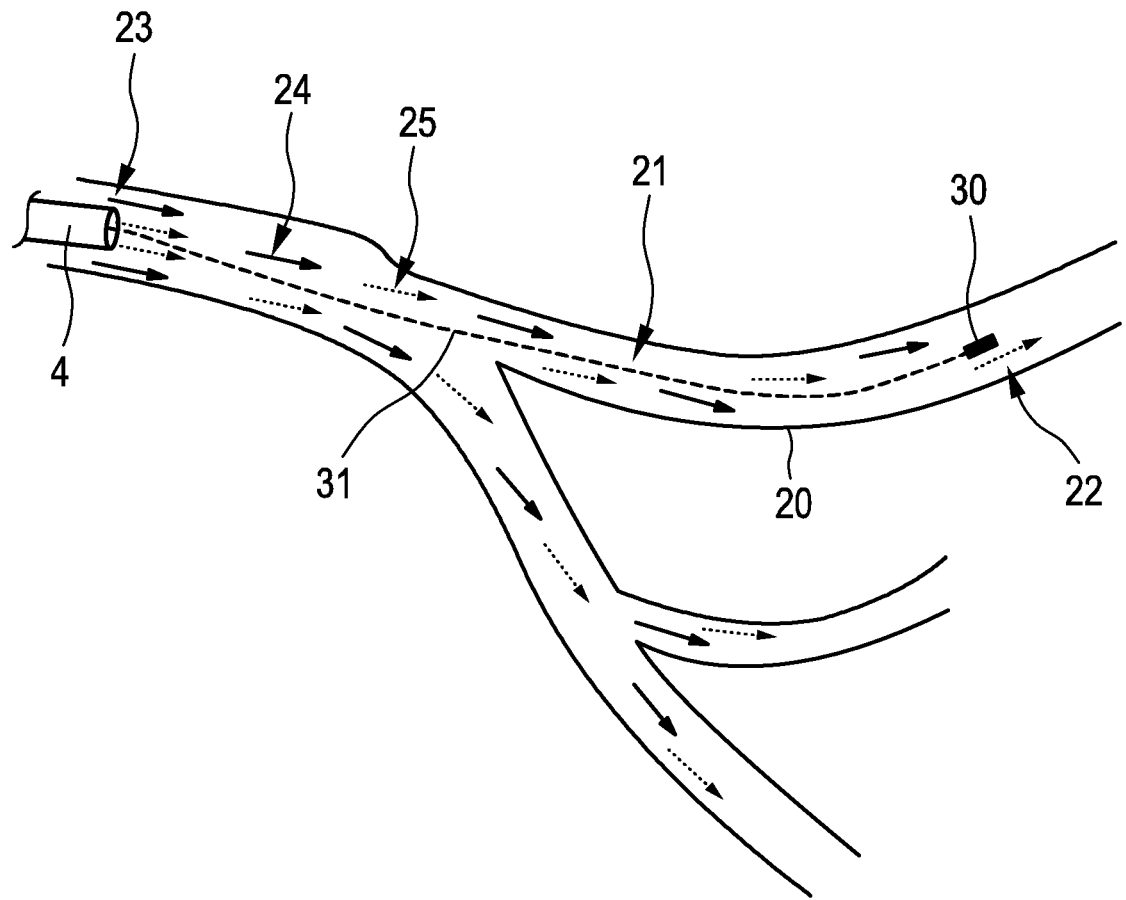
FIG. 2 shows schematically and exemplarily a distal end of a tube for introducing a fluid into a blood vessel and an IVUS probe within the blood vessel.

The angiography image generation system 1 further comprises a tube 4 which is preferentially a catheter and which is connected to a fluid pump 9, in order to introduce a fluid into a blood vessel 20 as schematically and exemplarily illustrated in FIG. 2. In FIG. 2 the arrows 25 indicate the flow of the introduced fluid and the arrows 24 indicate the flow of the blood within the inner lumen 21 of the blood vessel 20. Since the tube 4 and the fluid pump 9 are adapted to introduce the fluid into the blood vessel 20, the tube 4 and the fluid pump 9 can be regarded as being components of a fluid introduction unit.

The introduced fluid is a contrast agent such that the x-ray signals generated by the x-ray device 40 are indicative of the contrast agent within the blood vessel 20. The angiography image generation system 1 further comprises an x-ray signals processing unit 11 for processing the x-ray signals such that an angiography image is generated which shows the contrast agent within the blood vessel 20. The x-ray signals processing unit 11 can be adapted to use known computed tomography reconstruction techniques for generating the angiography image. However, the x-ray signals processing unit 11 can also be adapted to just provide a two-dimensional projection image as the angiography image in which the contrast agent is shown within the blood vessel 20. Since the x-ray device 40 and the x-ray signals processing unit 11 are adapted to generate the angiography image showing the contrast agent, the x-ray device 40 and the x-ray signals processing unit 11 can be regarded as being components of a contrast agent imaging unit.

The angiography image generation system 1 further comprises an IVUS probe 30 attached to a distal tip of a guiding element 31 being preferentially a guidewire. The IVUS probe 30 generates ultrasound signals which are processed by an ultrasound signals processing unit 10 such that an ultrasound image can be generated at an imaging location 22 at which the IVUS probe 30 is located. The imaging location 22 is arranged behind an introduction location 23, at which the fluid is introduced into the blood vessel 20, with respect to the blood flow direction 24. Since the IVUS probe 30 and the ultrasound signals processing unit 10 are adapted to generate an ultrasound image of the inner lumen 21 of the blood vessel 20 at the imaging location 22, the IVUS probe 30 and the ultrasound signals processing unit 10 can be regarded as being components of an ultrasound unit for generating an ultrasound image of an inner lumen of the blood vessel at the imaging location.

Figure 3:
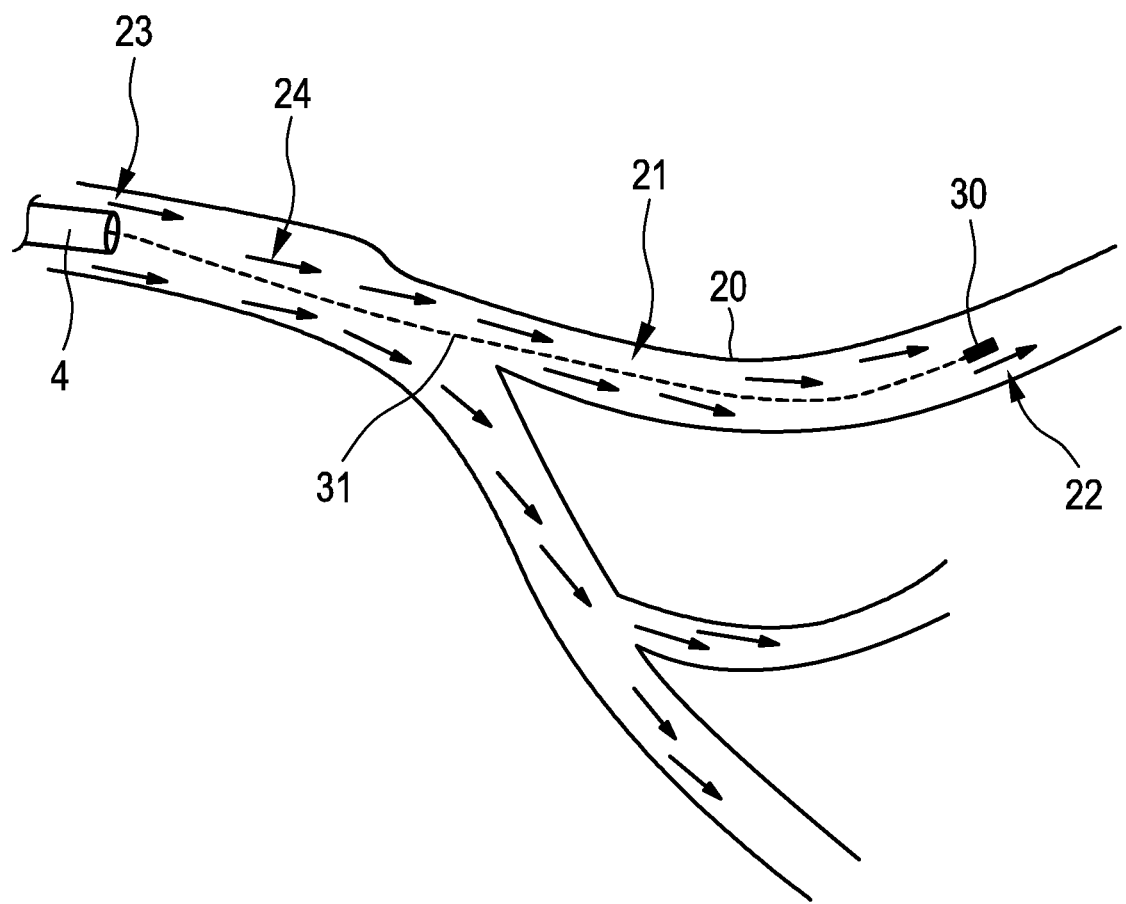
FIG. 3 shows schematically and exemplarily the distal end of the tube and the IVUS probe before introducing the fluid into the blood vessel.

The angiography image generation system 1 further comprises a speckle density providing unit 6 for providing a blood speckle density value being indicative of the level of the speckle density in an ultrasound image only showing blood and for providing a fluid speckle density value being indicative of the level of the speckle density in an ultrasound image only showing the fluid. In this embodiment the fluid speckle density value is stored in the speckle density providing unit 6 such that the speckle density providing unit 6 can just provide the stored fluid speckle density value. Also the blood speckle density value can be stored in the speckle density providing unit 6 such that also this value can be provided by the speckle density providing unit 6. However, the speckle density providing unit 6 can also be adapted to determine the blood speckle density value based on an ultrasound image showing an inner lumen of a blood vessel filled only with blood. In particular, the IVUS probe 30 and the ultrasound signals processing unit 10 can be adapted to generate an ultrasound image at the imaging location 22, before the fluid is introduced into the inner lumen 21 of the blood vessel 20. Such a situation, in which only blood flows within the blood vessel 20, is schematically and exemplarily illustrated in FIG. 3. Based on this ultrasound image the speckle density providing unit 6 can determine the blood speckle density value.

The angiography image generation system 1 further comprises a speckle density determination unit 7 for determining a speckle density value being indicative of a level of a speckle density in an ultrasound image of the inner lumen 21 of the blood vessel 20 which has been generated at the imaging location 22, after the fluid has been introduced into the blood vessel 20 at the introduction location 23. The speckle density value determined by the speckle density determination unit 7 is therefore a speckle density value being indicative of a level of a speckle density in an ultrasound image showing a mixture of the blood and the introduced fluid. Preferentially, the fluid pump 9 continuously introduces the fluid into the blood vessel 20 with a volumetric fluid flow rate which is preferentially constant. The IVUS probe 30 and the ultrasound signals processing unit 10 can be adapted to generate several ultrasound images over time at the imaging location 22, while the fluid is continuously introduced into the blood vessel 20. Moreover, the speckle density determination unit 7 can be adapted to determine the speckle density value such that it is indicative of an average of levels of speckle densities in some or all of these ultrasound images which have been generated for different times at the imaging location 22, while the fluid has been continuously introduced into the blood vessel 20. Thus, the speckle density determination unit 7 can be adapted to determine the speckle density value such that it corresponds to a temporal average. Moreover, the speckle density determination unit 7 is preferably adapted to consider the entire region of the respective ultrasound image, which corresponds to the inner lumen 21 of the blood vessel 20, for determining the speckle density value. The speckle density value can therefore also be regarded as being a spatial average value.

The angiography image generation system further comprises a blood flow rate determination unit 8 for determining a blood flow value being indicative of a volumetric blood flow rate based on the determined speckle density value and the volumetric fluid flow rate with which the fluid is introduced into the blood vessel 20. Preferentially, the blood flow rate determination unit 8 is adapted to use a non-linear relation between the blood flow value to be determined and the speckle density value. In particular, the blood flow rate determination unit 8 is adapted to use following equation as the non-linear relation between the blood flow value to be determined and the speckle density value:

$$Q_B = Q_C (f(d_M) - f(d_C))/(f(d_B) - f(d_M))$$

wherein $Q_B$ denotes the blood flow value to be determined, $Q_C$ denotes the volumetric fluid flow rate at the introduction location, $d_M$ denotes the speckle density value being indicative of the level of the speckle density in the ultrasound image of the inner lumen of the blood vessel which has been generated at the imaging location, $d_C$ denotes the provided fluid speckle density value, $d_B$ denotes the provided blood density speckle value, and f(d) denotes a non-linear function relating an ultrasound speckle density value d to a corresponding scatterer concentration.

The used speckle density value can be, as mentioned above, obtained by spatial and temporal averaging. The determination of the blood flow value based on the spatial and temporal averaging can make this determination more robust against incomplete mixing and independent of the placement of the IVUS probe within the blood vessel.

Since the speckle density providing unit 6, the speckle density determination unit 7 and the blood flow rate determination unit 8 are adapted to determine the blood flow value being indicative of the volumetric blood flow rate, these units can be regarded as being units of a blood flow determination apparatus 5. Moreover, this blood flow determination apparatus 5 together with the fluid introduction unit 4, 9 and the ultrasound unit 10, 30 can be regarded as being components of a blood flow determination system which in turn can be regarded as being a component of the angiography image generation system 1.

The system 1 further comprises an input unit 12 like a keyboard, a computer mouse, a touchpad et cetera for, for instance, entering a start or stop command for starting or stopping the procedure for determining the blood flow value or for providing another input to the system 1. Moreover, the system 1 comprises a display 13 for showing the determined blood flow value and the generated angiography image.

Figure 4:
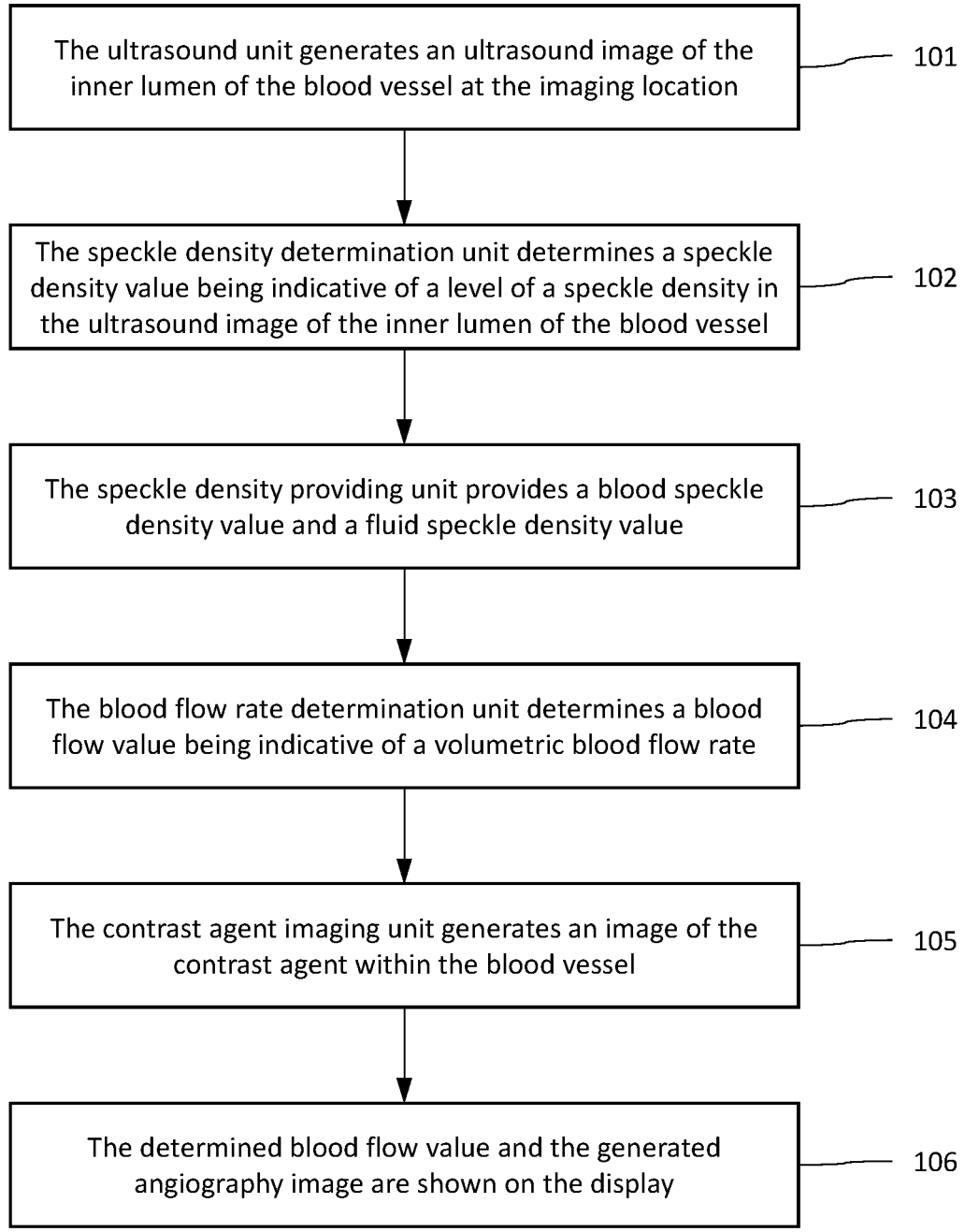
FIG. 4 shows a flowchart exemplarily illustrating an embodiment of an angiography image generation method for generating an angiography image.

In the following an embodiment of an angiography image generation method for generating an angiography image will be exemplarily described with reference to a flowchart shown in FIG. 4.

While continuously introducing the fluid into the blood vessel 20 with a constant volumetric fluid flow rate at the introduction location 23 by using the fluid introduction unit 4, 10, in step 101 the ultrasound unit 10, 30 generates an ultrasound image of the inner lumen 21 of the blood vessel 20 at the imaging location 22. In step 102 the speckle density determination unit 7 determines a speckle density value being indicative of a level of a speckle density in the ultrasound image of the inner lumen 21 of the blood vessel 20, which has been generated at the imaging location 22 in step 101. In step 103 the speckle density providing unit 6 provides a blood speckle density value and a fluid speckle density value, and in step 104 the blood flow rate determination unit 8 determines a blood flow value being indicative of a volumetric blood flow rate based on the speckle density value determined in step 102, the blood speckle density value and the fluid speckle density value provided in step 103 and the volumetric fluid flow rate with which the fluid is continuously introduced into the blood vessel 20.

The introduced fluid is a contrast agent and in step 105 the contrast agent imaging unit 11, 40 generates an image of the contrast agent within the blood vessel 20, in order to generate an angiography image. In step 106 the determined blood flow value and the generated angiography image are shown on the display 13.

Steps 101 to 104 can be regarded as being steps of a blood flow determination method. Moreover, the sequence of the steps can be different. For instance, step 105 can be performed at any time before step 106, as long as the contrast agent is within the blood vessel 20. Moreover, step 103 might be performed between steps 101 and 102 or before step 101.

The system and method described above with reference to FIGS. 1 to 4 allow for a determination of intravascular volumetric blood flow, i.e. the intravascular volumetric blood flow rate, based on the ultrasound speckle concentration, i.e. the level of the speckle density in an ultrasound image, in blood infused with a fluid being a contrast agent. The speckle density value being indicative of the level of the speckle density in the ultrasound image can be determined by using the intra-arterial signal strength of intravascular ultrasound.

The intravascular determination of blood flow volume, i.e. of the volumetric blood flow rate, provides important insights for examining the hemodynamic system. Particularly for assessing the functional impact of a coronary artery stenosis and for diagnosing the state of the coronary microvasculature the intravascular flow determination is very useful.

The angiography image can be used to determine the geometry of the blood vessel, i.e., for instance, the x-ray signals processing unit or another unit can be adapted to determine the geometry of the blood vessel based on the generated angiography image. Also the ultrasound images generated by using the IVUS probe can be used to determine the geometry of the blood vessel, especially of vessel cross sections and of the vessel wall. The ultrasound images can also be used to determine geometrical information about an expanded stent after it has been inserted during an interventional procedure. This geometrical information, which can be determined based on the ultrasound images, can be determined by the ultrasound signals processing unit or by another unit. The geometrical information obtained from the angiography image and/or the geometrical information obtained from the ultrasound images can be used for intravascular navigation, for diagnosis and/or for treatment planning The system and method described above with reference to FIGS. 1 to 4 allow for a determination of a blood flow value being indicative of a volumetric blood flow rate based on changes in an IVUS signal, i.e. in an ultrasound image generated by using an IVUS probe, during the infusion of the contrast agent. The intensity of the IVUS signal, i.e. the image values of the ultrasound image generated by using the IVUS probe, in blood depends on the ultrasound scatterer concentration within the blood. The infusion of the contrast agent with a lower or higher scatterer concentration than blood changes the overall scatterer concentration of the blood/contrast agent mixture and hence the speckle density in the corresponding ultrasound image, wherein this change can be used for determining the blood flow value being indicative of the volumetric blood flow rate as described above with reference to FIGS. 1 to 4.

Figure 5:
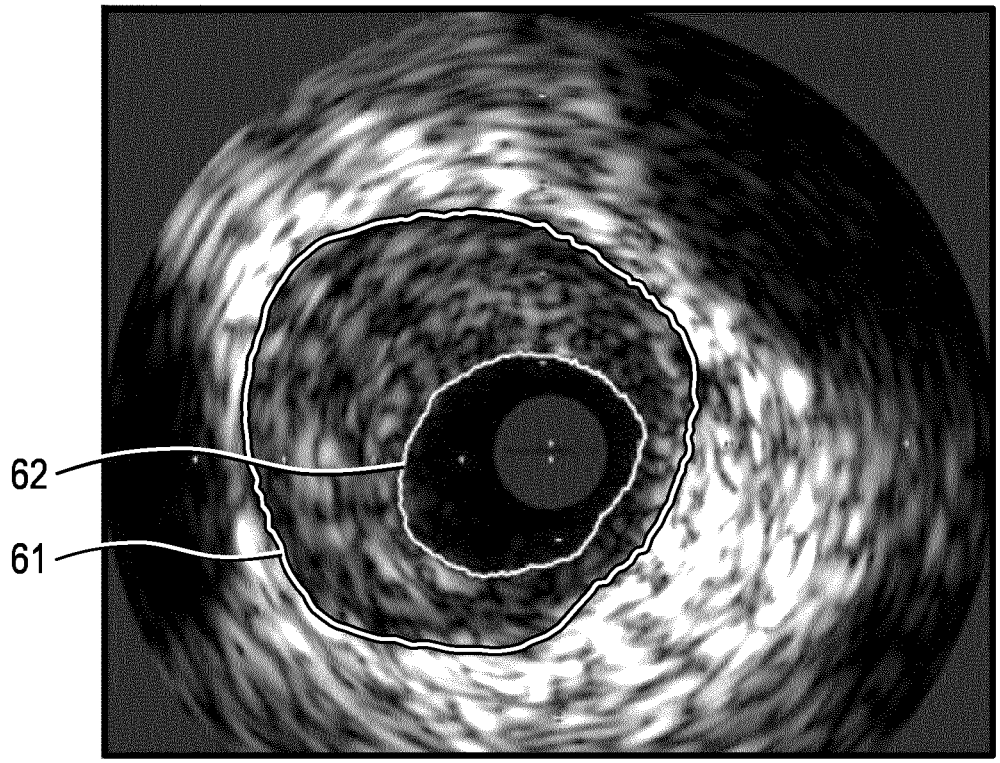
FIG. 5 shows schematically and exemplarily an ultrasound image of an inner lumen of a blood vessel.

FIG. 5 shows schematically and exemplarily an ultrasound image generated by the ultrasound unit, wherein in this ultrasound image a first line 61 indicates a border between a vessel wall and a plaque area and a second line 62 indicates a border between the plaque area and the inner lumen. The speckle density determination unit is preferentially adapted to determine a speckle density value being indicative of a level of speckle density based on the region of the respective ultrasound image which is enclosed by the second line 62. The speckle density determination unit can be adapted to automatically or semi-automatically segment the inner lumen of the blood vessel, i.e. to generate the second line 62, and to then determine the speckle density value based on the part of the ultrasound image within the second line 62.

Although in above described embodiments for determining the volumetric blood flow rate a contrast agent has been used which is visible in an x-ray image, in another embodiment another fluid can be used for determining the volumetric blood flow rate. For instance, saline can be used as fluid for determining the volumetric blood flow rate. Since saline substantially does not show speckles in an ultrasound image, in this case the fluid speckle density value $d_C$ can be zero. The mixing ratio of saline in blood defines the combined ultrasound scatterer concentration, i.e. the speckle density value being indicative of the level of speckle density in the ultrasound image of the inner lumen of the blood vessel, which has been generated at the imaging location being behind the introduction location with respect to the flow direction of the blood within the blood vessel. In particular, the speckle density value can be determined as the echogenicity of the ultrasound image, which is preferentially an IVUS image, inside the inner lumen of the blood vessel. The blood flow rate determination unit can then determine the volumetric blood flow rate based on a known saline injection rate, i.e. the known volumetric saline flow rate, and the ultrasound-based concentration or density measurement, i.e. the speckle density value.

Figure 6:
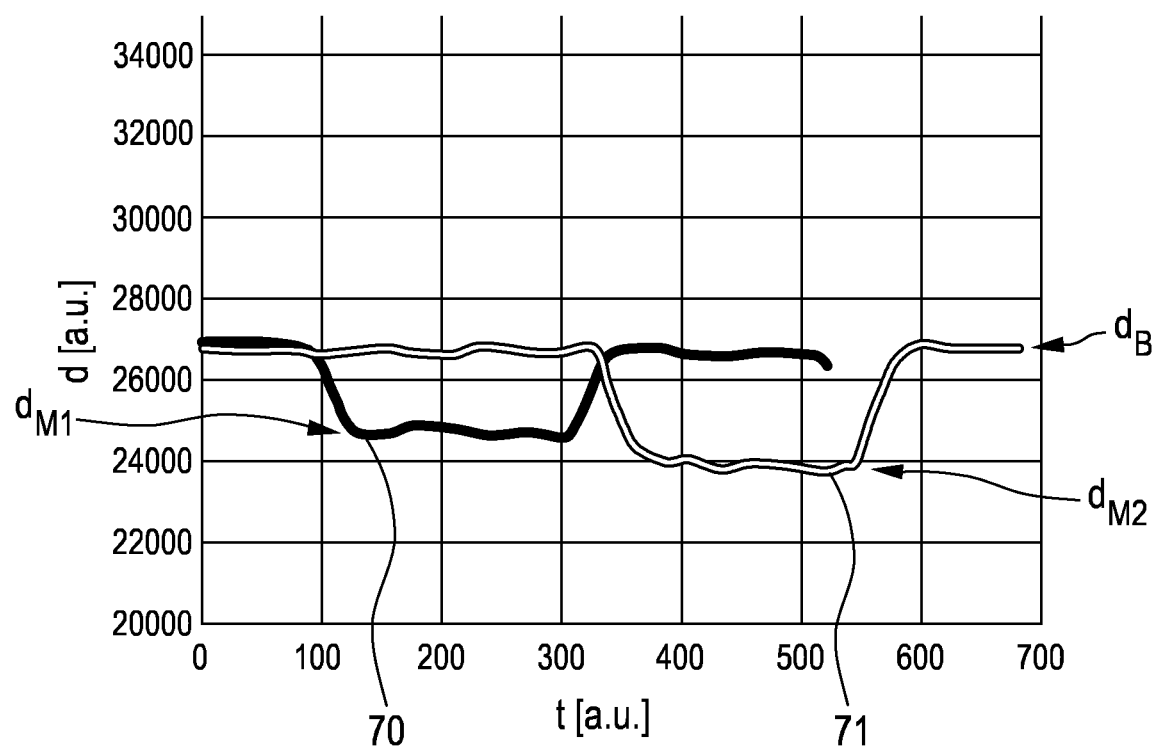
FIG. 6 illustrates schematically and exemplarily a speckle density over time for two different volumetric blood flow rates.
Figure 7:
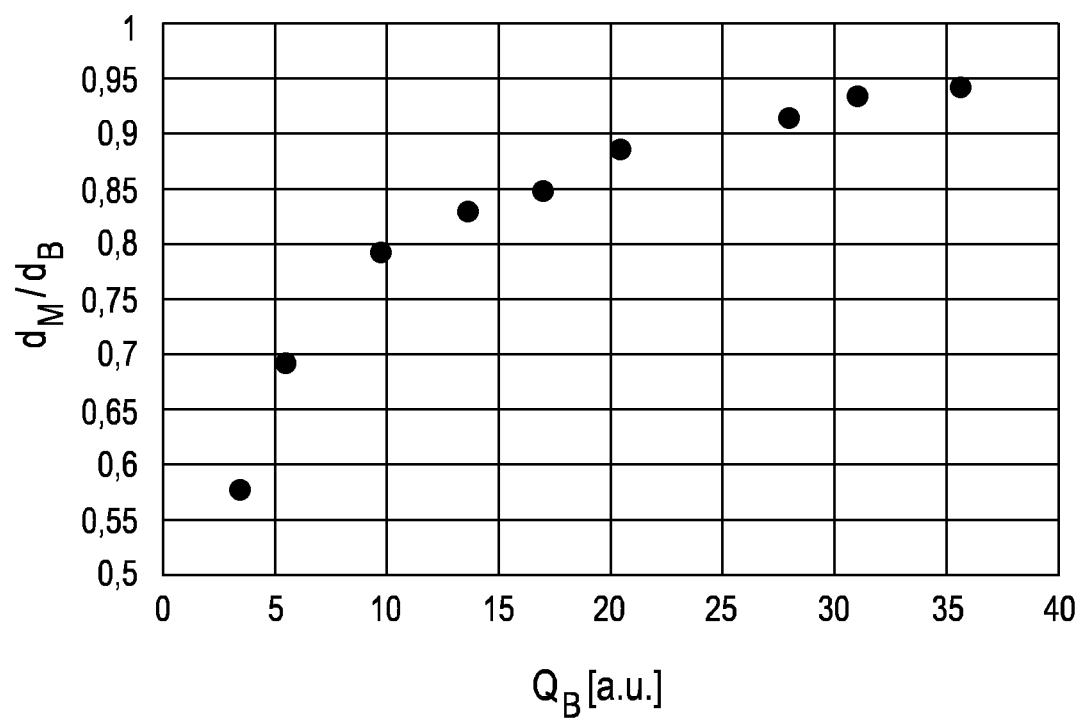
FIG. 7 illustrates schematically and exemplarily a dependence of a ratio of a) a speckle density value being indicative of a level of a speckle density of a mixture of blood and saline and b) a blood speckle density value being indicative of a level of a speckle density of blood on a blood flow value to be determined.

FIG. 6 shows schematically and exemplarily speckle density d in arbitrary units over time t in arbitrary units for two different volumetric blood flow rates. In this figure the line 70 corresponds to a larger volumetric blood flow rate and the line 71 corresponds to a smaller volumetric blood flow rate, wherein the fluid is saline and before and after the introduction of the saline fluid the speckle density value is the blood speckle density value $d_B$. For the first line 70 the speckle density value $d_{M1}$, of the mixture of the saline fluid and the blood indicates a level being larger than the level of the speckle density indicated by the speckle density value $d_{M2}$ of the second case illustrated by the second line 71. As is illustrated in this figure, in accordance with the invention the level or depth of the speckle density is used for determining the volumetric blood flow rate. In this embodiment, the respective speckle density value is determined by averaging the image values of the respective ultrasound image located within a region of the ultrasound image which corresponds to the inner lumen of the blood vessel. The speckle density is therefore an average echogenicity signal.

Although in an above described embodiment the blood flow rate determination unit is adapted to use a non-linear relation between the blood flow value to be determined and the speckle density value, particularly a certain non-linear equation, in other embodiments also other relations between the blood flow rate to be determined and the speckle density value can be used for determining the blood flow value being indicative of the volumetric blood flow rate. For instance, a relation between a) the ratio between i) the speckle density value $d_M$ being indicative of the level of the speckle density in the ultrasound image of the inner lumen of the blood vessel showing the mixture of the fluid and the blood and ii) the blood speckle density value $d_B$ and b) the blood flow value $Q_B$ to be determined can be used, particularly as schematically and exemplarily illustrated in FIG. 6. For example, for each volumetric fluid flow rate, with which the fluid is introduced into the blood vessel, a respective relation between this ratio and the blood flow value to be determined can be provided and the respective relation, which has been determined for the respective volumetric fluid flow rate, can be used together with the determined speckle density value $d_M$ and the known blood speckle density value $d_B$ for determining the blood flow value $Q_B$.

In above described embodiments the inflow of the fluid is controlled in relation to the blood flow, i.e. the fluid is introduced into the blood vessel with a known volumetric fluid flow rate. This can lead to a reduction of the speckle density value in the ultrasound image, i.e. to a drop of the speckle density value. Based on this reduced speckle density value the blood flow rate can be determined. Thus, the speckle density value can be determined based on how deep the measured speckle density curve is, i.e. the level of the speckle density in the ultrasound image can be determined, in order to provide the speckle density value, without looking how wide the curve is. For instance, for determining the blood flow value not the width of the broad minima of the lines 70, 71 shown in FIG. 5 is used, but the depths or levels of these minima.

Although in above described embodiments the angiography image generation system comprises an x-ray device with a C-arm for generating the angiography image, in other embodiments another x-ray device can be used for generating the angiography image like a computed tomography device.

Although in above described embodiments the same fluid is used for generating the angiography image and for determining the blood flow value, in other embodiments different fluids can be used for performing these tasks, i.e., for instance, a first fluid being a contrast agent can be used for generating the angiography image and a second fluid like saline can be used for determining the blood flow value.

Although in above described embodiments the blood flow determination is combined with angiography, the blood flow determination can also be carried out separately, i.e. without carrying out an angiography procedure. In particular, the blood flow determination apparatus and the blood flow determination system can be stand-alone systems which do not need to be integrated with another system like the angiography image generation system.

Figure 8:
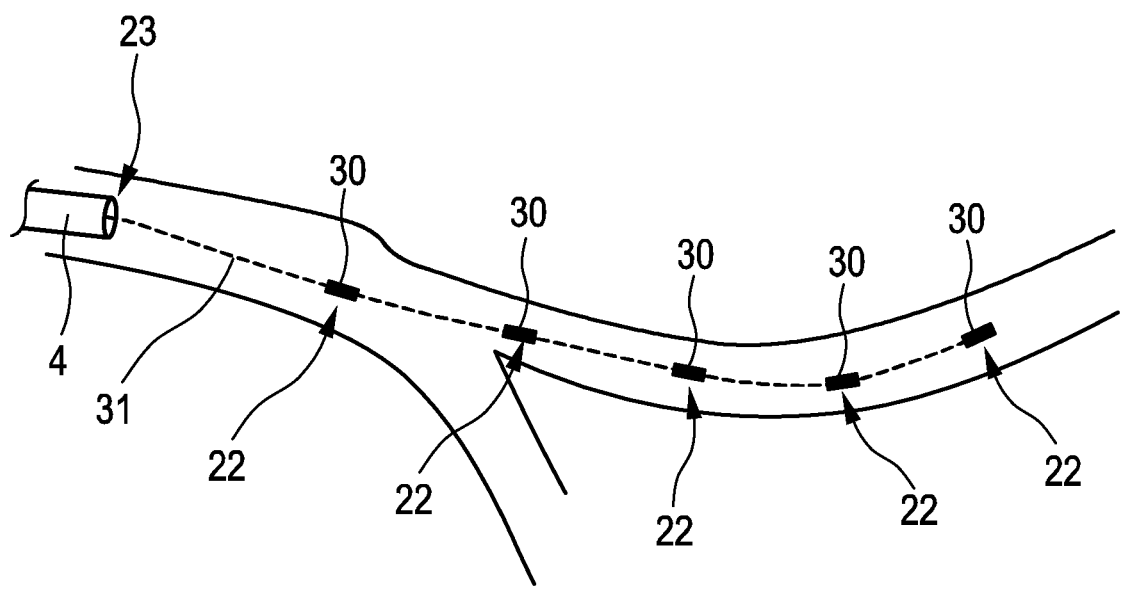
FIG. 8 shows schematically and exemplarily several IVUS probes within a blood vessel.

Although in above described embodiments the ultrasound unit comprises a single IVUS probe only, in other embodiments the ultrasound unit can comprise several IVUS probes 30 for generating several ultrasound images of the inner lumen 21 of the blood vessel 20 at several imaging locations 22 being behind the introduction location 23 with respect to the flow direction 24 of the blood within the blood vessel 20 as schematically and exemplarily illustrated in FIG. 8. In this case the speckle density determination unit 7 can be adapted to determine several speckle density values being indicative of the levels of the speckle densities of the respective ultrasound images and the blood flow rate determination unit 8 can be adapted to determine a blood flow value being indicative of the volumetric blood flow rate based on an average of the determined several speckle density values and the volumetric fluid flow rate with which the fluid is introduced into the blood vessel. This can further improve the quality of the determined blood flow value.

Figure 9:
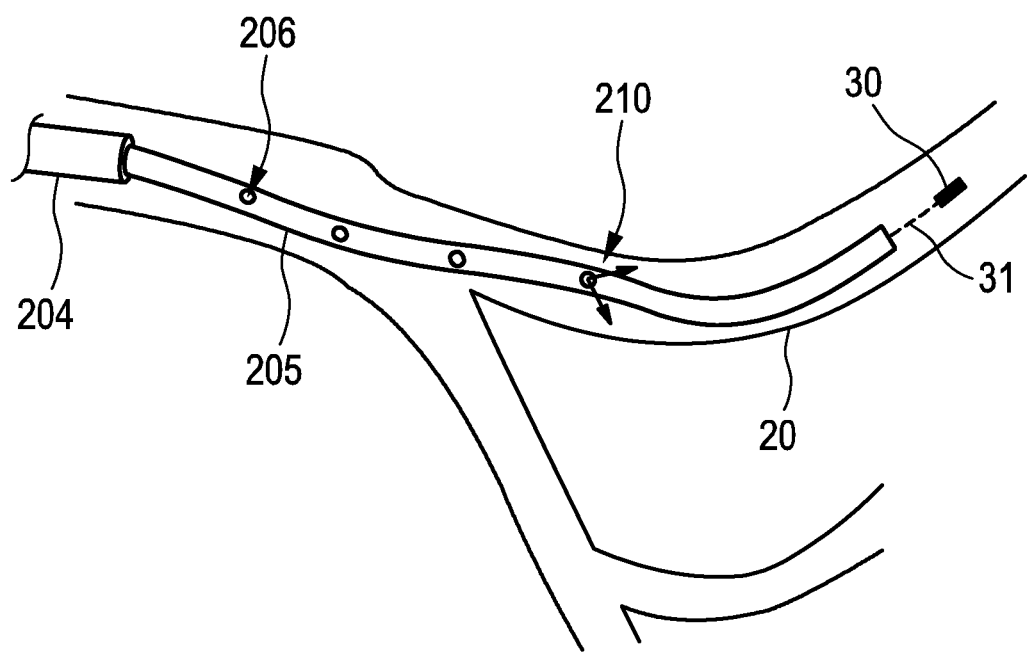
FIGS. 9 and 10 show schematically and exemplarily an embodiment of a tube for introducing the fluid into the blood vessel at several introduction locations.
Figure 10:
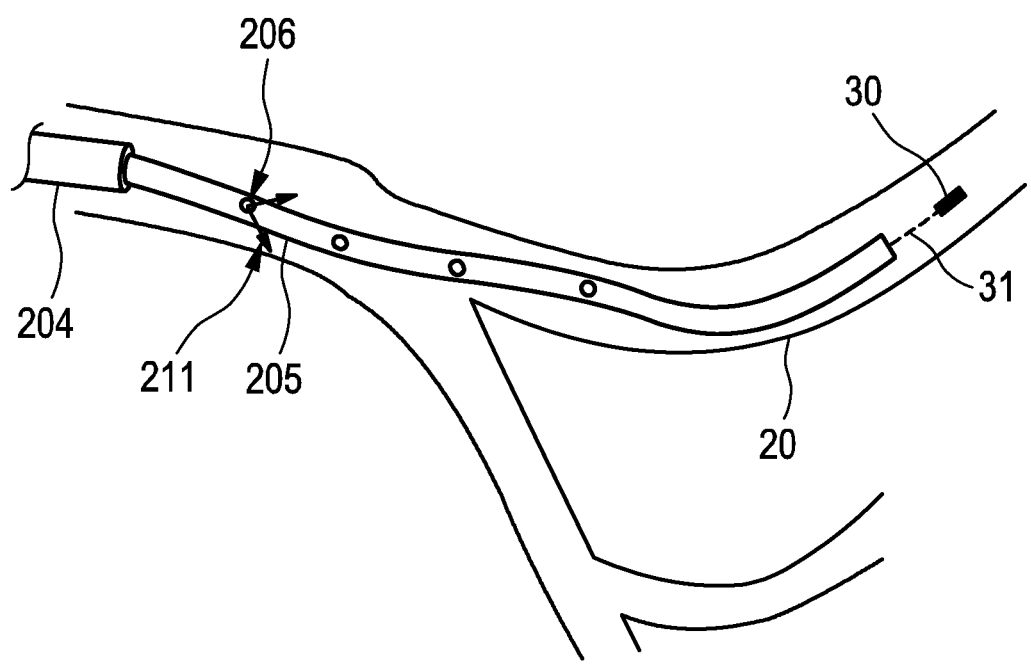

In a further embodiment the introduction unit comprises an outer tube 204, which is preferentially a catheter, and an inner tube 205, which might have a stiffness being smaller than the stiffness of the outer tube 204, as schematically and exemplarily shown in FIGS. 9 and 10. The inner tube 205 can be moved out of a distal opening of the outer tube 204 and comprises several tube openings 206 located along the length of the inner tube 205 for introducing the fluid into the blood vessel 20 at several introduction locations with a respective known volumetric fluid flow rate. At each introduction location the respective known volumetric fluid flow rate can be the same. However, it is also possible that the volumetric fluid flow rate is different at different introduction locations.

Each tube opening 206 can be connected to a respective fluid pump via a respective further tube within the inner tube 205, in order to provide the fluid at the respective tube opening 206 and hence at the respective introduction location.

Within the outer tube 204 and the inner tube 205 a guiding element 31 being preferentially a guidewire is located, wherein an IVUS probe 30 is attached to a distal tip of the guiding element 31. The IVUS probe 30 is used for generating an ultrasound image of the inner lumen of the blood vessel 20 at an imaging location being behind all introduction locations 206 with respect to the flow direction of the blood within the blood vessel 20. In this embodiment the fluid pumps are adapted to temporarily sequentially introduce the fluid into the blood vessel 20 at the different introduction locations, in order to allow for a generation of a respective ultrasound image by using the IVUS probe 30, which is influenced by the introduction of the fluid at the respective introduction location only. In this way for each introduction location a respective ultrasound image can be generated.

In FIG. 9 the arrows 210 indicate the introduction of the fluid into the blood vessel 20 at a first introduction location such that in this situation the IVUS probe 30 is used for generating an ultrasound image for this first introduction location. In FIG. 10 the arrows 211 indicate an introduction of the fluid at a second introduction location such that the ultrasound image generated by using the IVUS probe 30 corresponds to this second introduction location.

In this embodiment the speckle density determination unit 7 is adapted to determine for each ultrasound image a respective speckle density value being indicative of the level of the speckle density in the respective ultrasound image, i.e. for each ultrasound image and hence for each introduction location, a respective speckle density value is determined. The blood flow rate determination unit 8 is adapted to determine several blood flow values being indicative of several volumetric blood flow rates based on the determined several speckle density values and the respective volumetric fluid flow rate. Thus, for each introduction location a volumetric blood flow rate is determined based on the speckle density value, which has been determined for the respective introduction location, and based on the volumetric fluid flow rate with which the fluid has been introduced into the blood vessel 20 at the respective introduction location.

Figure 11:
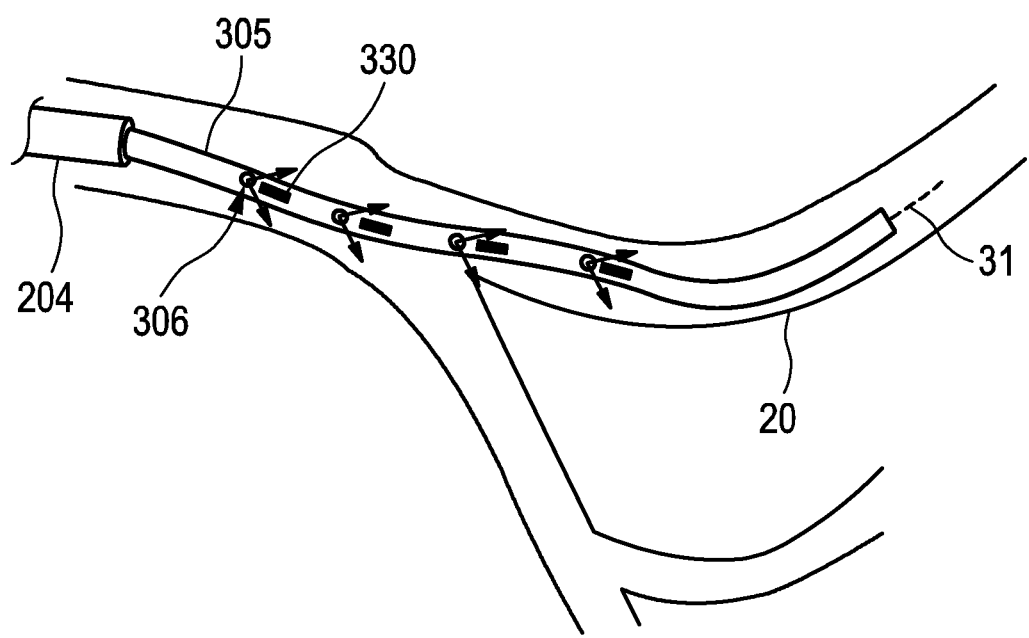
FIG. 11 shows schematically and exemplarily a further embodiment of a tube for introducing the fluid into the blood vessel at several introduction locations.

FIG. 11 schematically and exemplarily shows a further embodiment of an inner tube 305 within the outer tube 204, which is preferentially a catheter, wherein the inner tube 305 can be moved out of the outer tube 204 such that a distal part of the inner tube 305 is outside of the outer tube 204. Also in this embodiment the inner tube 305 comprises several tube openings 306 located along the length of the tube 305 for introducing the fluid into the blood vessel 20 at several introduction locations with a respective known volumetric fluid flow rate. Moreover, also in this embodiment the inner tube 305 can have a stiffness being lower than the stiffness of the outer tube 204. Furthermore, also in this embodiment each tube opening 306 can be connected to a respective fluid pump via a respective tube inside the inner tube 305, in order to provide the fluid at the different tube openings 306. Within the inner tube 305 a guiding element 31 being preferentially a guidewire is arranged. Behind each tube opening 306 a respective IVUS probe 330 is arranged for generating ultrasound images at imaging locations behind the respective introduction locations.

The speckle density determination unit 7 is adapted to determine for each ultrasound image a respective speckle density value being indicative of the level of the speckle density in the respective ultrasound image such that for each imaging location a respective speckle density value is determined. The blood flow rate determination unit 8 is adapted to determine several blood flow values being indicative of several volumetric blood flow rates based on the determined several speckle density values and the volumetric fluid flow rates. In particular, for a respective introduction location a respective blood flow value is determined based a) on the speckle density value of the ultrasound image generated at the imaging location immediately behind the respective introduction location, b) on the respective volumetric fluid flow rate with which the fluid has been introduced into the blood vessel at the respective introduction location and, if introduction locations are present in front of the respective introduction location, c) also on the volumetric fluid flow rates with which the fluid has been introduced into the blood vessel at the previous introduction locations.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

Operations like the determination of a speckle density value, the determination of a blood flow value, et cetera performed by one or several units or devices can be performed by any other number of units or devices. These operations and/or the control of the angiography image generation system in accordance with the angiography image generation method and/or the control of the blood flow determination apparatus in accordance with the blood flow determination method can be implemented as program code means of a computer program and/or as dedicated hardware.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The invention relates to a blood flow determination apparatus comprising a speckle density determination unit for determining a speckle density value being indicative of a level of a speckle density in an ultrasound image of an inner lumen of a blood vessel, which has been generated at an imaging location being behind an introduction location at which a fluid has been introduced into the blood vessel with a known volumetric fluid flow rate. A blood flow rate determination unit determines a blood flow value being indicative of a volumetric blood flow rate based on the determined speckle density value and the volumetric fluid flow rate. This allows determining the intravascular blood flow with an improved accuracy.

The invention claimed is:

1. A blood flow determination method comprising: determining a speckle density value indicative of a level of a speckle density in a first ultrasound image of an inner lumen of a blood vessel at an imaging location, wherein the imaging location is behind an introduction location with respect to a flow direction of blood within the blood vessel, wherein the introduction location corresponds to a fluid that is introduced into the blood vessel with a volumetric fluid flow rate that is known;
    determining a blood speckle density value indicative of the level of the speckle density in a second ultrasound image only showing blood;
    determining a fluid speckle density value indicative of the level of the speckle density in a third ultrasound image only showing the fluid;
    determining a blood flow value indicative of a volumetric blood flow rate based on a relation including three or more values of a plurality of values, wherein the plurality of values comprises the speckle density value, [[and]] the volumetric fluid flow rate, the blood speckle density value, and the fluid speckle density value, wherein the speckle density value is directly used in the relation; and
    displaying the blood flow value.

2. The method of claim 1, wherein the speckle density value is indicative of an average of levels of speckle densities in at least some of several ultrasound images which have been generated for different times at the imaging location, while the fluid is continuously introduced into the blood vessel.

3. The method of claim 1, wherein determining the speckle density value is based on an entire region of the first ultrasound image.

4. The method of claim 1, further comprising:
    generating several ultrasound images of the inner lumen of the blood vessel at several imaging locations, wherein the several imaging locations are behind the introduction location with respect to the flow direction of the blood within the blood vessel;
    determining several speckle density values being indicative of levels of the speckle densities of respective ultrasound images; and
    determining the blood flow value based on the volumetric fluid flow rate and an average of the determined several speckle density values.

5. The method of claim 1, wherein the relation comprises a non-linear relation between the blood flow value to be determined and the speckle density value.

6. The method of claim 5, wherein the relation comprises:

$Q_B = Q_C (f(d_M) - f(d_C)) / (f(d_B) - f(d_M))$, wherein:

$Q_B$ denotes the blood flow value to be determined,
$Q_C$ denotes the volumetric fluid flow rate,
$d_M$ denotes the speckle density value,
$d_C$ denotes the fluid speckle density value, $d_B$ denotes the blood density speckle value, and
f(d) denotes a non-linear function relating an ultrasound speckle density value d to a corresponding scatterer concentration.

7. The method of claim 1, further comprising:
    generating the first ultrasound image.

8. The method of claim 7, wherein generating the first ultrasound image comprises:
    generating an intravascular ultrasound (IVUS) image.

9. The method of claim 1, wherein introducing the fluid comprises introducing the fluid at several introduction locations with a respective volumetric fluid flow rate that is known, using a tube with several tube openings located along a length of the tube.

10. The method of claim 9, further comprising:
    determining, for each introduction location, a respective ultrasound image of the inner lumen of the blood vessel at a respective imaging location, wherein the respective imaging location is behind a respective introduction location with respect to the flow direction of the blood within the blood vessel;
    determining, for each respective ultrasound image, a respective speckle density value indicative of the level of the speckle density in its respective ultrasound image; and
    determining several blood flow values indicative of several volumetric blood flow rates based on several speckle density values and several volumetric fluid flow rates.

11. The method of claim 1, wherein the fluid comprises a contrast agent.

12. The method of claim 11, further comprising:
    generating an angiography image showing the contrast agent; and displaying the angiography image.

13. A blood flow determination method comprising:
    determining a speckle density value indicative of a level of a speckle density in a first ultrasound image of an inner lumen of a blood vessel at an imaging location, wherein the imaging location is behind an introduction location with respect to a flow direction of blood within the blood vessel, wherein the introduction location corresponds to a fluid that is introduced into the blood vessel with a volumetric fluid flow rate that is known;
    determining a blood speckle density value indicative of the level of the speckle density in a second ultrasound image only showing blood;
    determining a fluid speckle density value indicative of the level of the speckle density in a third ultrasound image only showing the fluid;
    determining a blood flow value indicative of a volumetric blood flow rate based on a relation including two or more values of a plurality of values, wherein the plurality of values comprises the speckle density value, the volumetric fluid flow rate, the blood speckle density value, and the fluid speckle density value, wherein a first value of the two or more values is the speckle density value, and wherein a second value of the two or more values is the blood speckle density value or the fluid speckle density value; and
    displaying the blood flow value.

14. The method of claim 13, wherein the speckle density value is indicative of an average of levels of speckle densities in at least some of several ultrasound images which have been generated for different times at the imaging location, while the fluid is continuously introduced into the blood vessel.

15. The method of claim 13, wherein determining the speckle density value is based on an entire region of the first ultrasound image.

16. The method of claim 13, further comprising:
generating several ultrasound images of the inner lumen of the blood vessel at several imaging locations, wherein the several imaging locations are behind the introduction location with respect to the flow direction of the blood within the blood vessel;
determining several speckle density values being indicative of levels of the speckle densities of respective ultrasound images; and
determining the blood flow value based on the volumetric fluid flow rate and an average of the determined several speckle density values.

17. The method of claim 13, wherein the relation comprises a non-linear relation between the blood flow value to be determined and the speckle density value.

18. The method of claim 17, wherein the relation comprises:

$$Q_B = Q_C (f(d_M) - f(d_C))/(f(d_B) - f(d_M)),$$

wherein:
$Q_B$ denotes the blood flow value to be determined,
$Q_C$ denotes the volumetric fluid flow rate,
$d_M$ denotes the speckle density value,
$d_C$ denotes the fluid speckle density value,
$d_B$ denotes the blood density speckle value, and
f(d) denotes a non-linear function relating an ultrasound speckle density value d to a corresponding scatterer concentration.

19. The method of claim 13, further comprising:
generating the first ultrasound image.

20. The method of claim 19, wherein generating the first ultrasound image comprises:
generating an intravascular ultrasound (IVUS) image.

21. The method of claim 13, wherein introducing the fluid comprises introducing the fluid at several introduction locations with a respective volumetric fluid flow rate that is known, using a tube with several tube openings located along a length of the tube.

22. The method of claim 21, further comprising:
determining, for each introduction location, a respective ultrasound image of the inner lumen of the blood vessel at a respective imaging location, wherein the respective imaging location is behind a respective introduction location with respect to the flow direction of the blood within the blood vessel;
determining, for each respective ultrasound image, a respective speckle density value indicative of the level of the speckle density in its respective ultrasound image; and
determining several blood flow values indicative of several volumetric blood flow rates based on several speckle density values and several volumetric fluid flow rates.

23. The method of claim 13, wherein the fluid comprises a contrast agent.

24. The method of claim 23, further comprising:
generating an angiography image showing the contrast agent; and
displaying the angiography image.

* * * * *